United States Patent [19]
Frank et al.

[11] Patent Number: 5,798,827
[45] Date of Patent: Aug. 25, 1998

[54] APPARATUS AND METHOD FOR DETERMINATION OF INDIVIDUAL RED BLOOD CELL SHAPE

[75] Inventors: Robert S. Frank, Pembroke Pines; James L. Wyatt, Plantation; Weiyan Gong; Carlos M. Rodriguez, both of Miami, all of Fla.; Robert C. Leif, San Diego, Calif.

[73] Assignee: Coulter International Corp., Miami, Fla.

[21] Appl. No.: 753,585

[22] Filed: Nov. 26, 1996

[51] Int. Cl.[6] .................... G01N 21/47; G01N 33/49
[52] U.S. Cl. .................. 356/39; 356/72; 356/336; 356/343
[58] Field of Search ................... 356/39, 72, 73, 356/336, 338, 343

[56] References Cited

U.S. PATENT DOCUMENTS

4,606,636  8/1986  Monin et al. ................. 356/338

*Primary Examiner*—Richard A. Rosenberger
*Attorney, Agent, or Firm*—Mitchell E. Alter

[57] ABSTRACT

The present invention provides an apparatus and method to determine individual red blood cell shape within a flow cytometric aperture. Cell shape is determined by measuring the asymmetry of a light scatter pattern produced by laser illumination of the cell within the aperture by light scatter detectors which collect light from specific angular regions of light scatter, and analyzing the asymmetry of the light scatter patters to determine the individual red blood cell shape. Embodiments of the invention further provide for the determination of red blood cell shape by measuring the asymmetry of a light scatter pattern and measuring electrical resistance of the red blood cell.

45 Claims, 9 Drawing Sheets

APPARATUS AND METHOD FOR DETERMINATION OF INDIVIDUAL RED BLOOD CELL SHAPE

FIELD OF THE INVENTION

The present invention relates to an apparatus and method for the determination of individual red blood cell shape, as the red blood cell passes through a flow cytometric measurement aperture. More specifically, the present invention relates to an apparatus and method for making shape determination, and for determining statistical characteristics of a blood sample containing a plurality of red blood cells and for identifying subpopulations of red blood cells in the sample.

BACKGROUND OF THE INVENTION

The determination of information concerning the red blood cells of a person is routinely performed for the monitoring of health of the individual and in the diagnosis of certain hematological diseases. Information about the red blood cell that are routinely determined include the number of cells per unit volume of whole blood (called the "Red Blood Count" or "RBC"); the amount of hemoglobin per unit volume of blood (Hemoglobin Content or [Hb]); the volume of each cell; the hemoglobin content of each cell; and the hemoglobin concentration of each cell.

For information which relate to individual cells, either a single measurement may be made on a plurality of cells to determine an average value for the population, or measurements may be made on a number of individual cells, with a mean value calculated from these multiple measurements. Measurements made on individual cells provide additional information to the mean value, in that it is possible to determine the distribution of the measurement in the population and to identify unusual subpopulations within the larger population. For example, determination of cell volume by individual cell measurements allows for the determination of a Red Cell Distribution Width (RDW) and Mean Cell Volume (MCV). Likewise, Mean Cell Hemoglobin (MCH), Mean Cell Hemoglobin Concentration (MCHC), and associated distributions can be determined from individual cell measurements of hemoglobin content and hemoglobin concentration.

Automated blood cell analyzers use a variety of electrical impedance and optical techniques to perform cellular measurements. In general, these measurements are dependent upon the shape and orientation of the cell while the measurements are made. Since the pioneering invention of Wallace Coulter of a technique to quantify cell number and volume by electrical means (U.S. Pat. No. 2,656,508, 1953), the influence of cell shape upon cell volume measurements has been studied. A correction for the shape of the cell on the electrical volume measurement was first described by Grover et al. (Grover, N. B., Naaman, J., Ben-Sasson, S., and Doljanski, F., "Electrical Sizing of Particles in Suspensions: I. Theory," *Biophysical Journal* 9: 1398–1414, 1969). This correction is known to those skilled in the art of cytometry as the "Shape Factor," which varies from 1.5 for a spherical cell to 1.0 for an elongated cell.

At rest, red blood cells are normally discoid in shape and very easy to deform. During flow, they deform into elongated shapes in response to fluid mechanical forces acting upon them. In general, red cells deformed in a flow field tend to orient with their long axis parallel to the direction of flow. The amount of deformation of red cells in response to these forces is determined by a multitude of material and geometric properties of the individual cell, including the internal viscosity of the cell, intrinsic stiffness and viscosity of its membrane, and the ratio of the membrane surface area to the volume of the cell.

Red blood cells flowing through a cytometric instrument experience fluid forces which cause significant and variable deformations of the red cells. In order to account for these variations in the shape of the red cell during cytometric measurements, instrument manufacturers have adopted several schemes. Many instruments are calibrated to assume a particular shape, and interpret all measurements based upon this assumption. This scheme can lead to inaccuracies, particularly for abnormal cell populations where the deformed cell shape is different from the shape of a normal population. Other instruments chemically sphere and stabilize the red cells prior to making measurements. This process avoids errors due to the heterogeneity of cell shapes, but information concerning cellular morphology and rheology is lost. Neither of the previous two schemes allows for both an accurate determination of cell volume and a determination of the native deformability of the cell.

In addition to the effect of red cell shape on cytometric measurements, there is growing evidence concerning the clinical importance of the deformability of the red cell in itself. It is believed that the ability of a red cell to deform in response to fluid mechanical forces has important consequences to the ability of the red cells to flow through the circulatory system and perform its function of oxygen delivery within the body.

Moreover, alterations in red cell deformability have been related to many disease processes. A number of specialized instruments have been developed that measure the deformability and shape of red blood cells. A review of these instruments is given by Boisseau (Boisseau, M., "New Trends in Current Implementation of Rheological Technologies for the Human Blood," *Clinical Hemorheology*, 16:27–30, 1996). Most commonly, these measurements are made either in viscometric apparatus, filtration devices, or with microscope based systems. In general, these instruments are specialized devices that do not measure the standard red cell properties, and thus, typically are not used in the clinical laboratory setting. Currently, there does not exist an instrument and method determines the shape or deformability of an individual red blood cell simultaneously with other cytometric measurements.

The principle of measuring the shape and deformation of red blood cells by light scatter was first taught by Bessis and Mohandas (U.S. Pat. No. 3,955,890, 1973). They recognized that while the scattering pattern of a spherical particle is circular in shape, the scattering patterns of elongated particles are ellipsoidal in shape. These patterns are oriented such that the long axis of the diffraction pattern is perpendicular to the long axis of the elongated particle. They taught that one could qualitatively observe the deformation of particles such as red cells by measuring the asymmetry of the light scatter pattern. They constructed an instrument, which they named the "Ektacytometer," which consisted of a Couette type viscometer fitted with a laser light source and a light scatter detector. A suspension of red blood cells was placed in the viscometer and caused to deform by the shear stress created by the rotation of the viscometer. Light from a laser was projected through this red cell suspension, producing a composite scattering pattern from the scatter of each individual cell illuminated. Typically, several hundred individual red blood cells scatter light at any instant in time in this apparatus. By monitoring the intensity of the scattered light at specific positions along the two orthogonal principal axes, a measure of the asymmetry of the pattern is determined. This measure, termed the deformability index (D.I.) of the pattern, qualitatively relates to the deformation of the cell population. Since the measurement is the average for the entire population illuminated at any one time, the precise correlation of the shape of the light scatter pattern with the actual shape of the red cells in the population was not possible.

Subsequently, Streekstra, et al. (Streekstra G. J., Hoekstra A. F., Nijhof E-J, and Heethaar R. M., "Light Scattering by Red Blood Cells in Ektacytometry: Fraunhofer versus Anomalous Diffraction," *Applied Optics* 32:2266–2272, 1993) reported a method to analyze the light scatter patterns in terms of the actual geometry of the deformed, red cell population. The improved method utilized video cameras in place of the simple light scatter detectors. However, this method still provides a measurement which is an average for the total population of cells illuminated at a given time.

A subsequent patent by Bessis (U.S. Pat. No. 4,428,669, 1984) describes the use of a capillary flow system to induce the deformation of red cells for a laser-based shape measurement. This system still relies upon the scattering from a population of cells, as opposed to a single cell, to produce the measurement.

The first description of a method to measure the shape of individual cells within a cytometric measurement aperture was taught by Groves et al. (U.S. Pat. No. 4,298,836, 1981). They recognized the utility of measuring cell shape for improving the accuracy of other cytometric determinations. The Groves et al. invention employed the technique known to those versed in the art of cytometry as "slit scanning." This technique measures the length of time a cell requires to cross a narrow slit of light and determines the length of the cell from this time measurement and the velocity of the cell. This method suffers from the problem that the velocity of a cell must be very accurately controlled to a known value. However, because it is difficult to precisely control the velocity at any moment in time, the use of slit scanning technique to determine cell length and cell shape has not been implemented on any known commercial instrument.

The prior art has failed to disclose the determination of an individual red cell shape by using light scatter asymmetry or by using light scatter asymmetry and electrical resistance. Consequently there exists a need for an apparatus and method to determine the shape of an individual red cell. Preferably, the apparatus and method enable other cytometric determinations concurrent with the shape determination.

SUMMARY OF THE INVENTION

In view of the foregoing, an object of the invention is to provide an improved apparatus and method to determine the shape of an individual red blood cell in a fluid sample by using light scatter which is independent of the index of refraction of the cell and independent of the volume of the cell. A further object of the invention is to provide an improved apparatus and method to determine the shape of an individual red blood cell in a fluid sample by using light scatter which is independent of the index of refraction of the cell and electrical resistance.

Accordingly, the present invention provides an apparatus and method for determining an individual red blood cell shape in a fluid sample, said apparatus comprising means for forming a stream of individual red blood cells in a fluid; means for flowing said stream of individual red blood cells through an aperture; means for illuminating said red blood cell with a beam of light while said cell flows through said aperture, which causes said light to be scattered; means for measuring intensity of said light scattered by said cell at a minimum of two different azimuthal angular regions, said light scatter at said angular regions being independent of the index of refraction of said cell and independent of cell volume; means for deriving a corresponding signal for each angular region, said signal having an amplitude representative of said intensity of light scattered in said angular region; and means for determining a shape of said red blood cell from said corresponding signal for each angular region.

According to a preferred embodiment of the apparatus and method, the invention further provides means for providing an electrical current flow through said aperture and means for measuring the resistance of said aperture to said current flow; means for measuring a change in said electrical resistance caused by a red blood cell in said stream of red blood cells flowing through said aperture; means for deriving a corresponding first signal having an amplitude representative of said change in said electrical resistance caused by said red blood cell flowing through said aperture; means for measuring intensity of said light scattered by said cell at a minimum of two different azimuthal angular regions, said light scatter at said angular regions being independent of the index of refraction of said cell; and means for determining a shape of said red blood cell from said corresponding first signal and said corresponding signal for each angular region.

The invention and its various advantages will be better understood from the ensuing detailed description of preferred embodiments, reference being made to the accompanying drawings in which like reference to characters drawn to like parts.

DETAILED DESCRIPTION OF THE PREFERRED EMBODIMENT

The present invention provides an apparatus and method which enables the rapid, accurate and economical determination of cell shape on a cell by cell basis within a cytometric measurement systems that heretofore has not been possible.

The apparatus of the invention for determining the shape of individual red blood cells in a fluid sample comprises fluidic system means for forming a stream of individual red blood cells in an electrolytic fluid and flowing said stream of individual red blood cells through a measurement aperture; means for producing an electrical current flow through said aperture and means for measuring the electrical resistance of said aperture to said current flow; means for measuring a change in electrical resistance caused by a red blood cell in said stream of red blood cells flowing through said aperture; means for deriving a corresponding first signal having an amplitude representative of said change in said electrical resistance caused by said red blood cell flowing through said aperture; means for illuminating said red blood cell with a beam of light while said cell flows through said aperture, which causes said light to be scattered; means for measuring intensity of said light scattered by said cell at a minimum of two different azimuthal angular regions; means for deriving a corresponding signal for each angular region, said signal having an amplitude representative of said intensity of light scattered in said angular region; and a means for determining a shape of said red blood cell from said corresponding first signal and said corresponding signal for each angular region.

The fluidic system comprises a means for forming a stream of individual red blood cells in an electrolytic fluid and flowing said stream of individual red blood cells through a measurement aperture is not shown in the accompanying figures as it is well known by those skilled in the art. It typically comprises a liquid stream of individually suspended blood cells, originally from a pressurized reservoir, which proceeds through a concentric tube. A laminar liquid sheath, originally from another pressurized reservoir, proceeds through the tube so as to surround the stream of individual blood cells. As the liquid stream of blood cells exits from the tube, hydrodynamic pressures reduce the diameter of the stream of cells as the stream obtains the velocity of the liquid sheath. The liquid sheath also acts to center the steam of cells so that particles pass through an orifice along a center axis, with the elongated cell axis aligned with the center axis.

A measurement aperture is more fully described herein, said aperture being used when measuring a change in electrical resistance caused by a red blood cell in said stream of red blood cells flowing through said aperture. Preferably, a constant current power source can be used as an electrical source to provide a low frequency or direct current electrical field imposed across the aperture. Therefore, a variation in electric resistance between the electrodes can be detected as a variation in voltage between electrodes.

Preferably, a monochromatic light source, such as a laser beam light source, is used as a means for illuminating the red blood cell when the red blood cell flows through the aperture. The red blood cell will cause the light to be scattered.

A photodiode, phototransistor, photomultiplier or the like can be used as a means for measuring intensity of the light scattered by the red blood cell. Preferable embodiments are provided herein.

The calculating means comprising a data processor or a microcomputer can be used as a means for determining a shape of the red blood cell from the electrical resistance and light scatter signals. Desirably, an appropriate display such as a cathode ray tube (CRT), printer or other display depicts the results of the calculations performed by the calculating means. Moreover, the calculating means can determine the average shape of a cell population and distribution of the shape population. Calculating means can also determine the deformability index of each cell, the average deformability index for the population, and the distribution of the deformability index in the population. In addition, the calculating means can determine an individual cell volume, average volume of a cell population, distribution of a volume population, and correlation of the volume for each cell within the population with the measurements obtained for cell shape.

The present invention will be detailed in conjunction with embodiments shown in the accompanying drawings, but they are not intended to limit the scope of the present invention.

Figure 1:
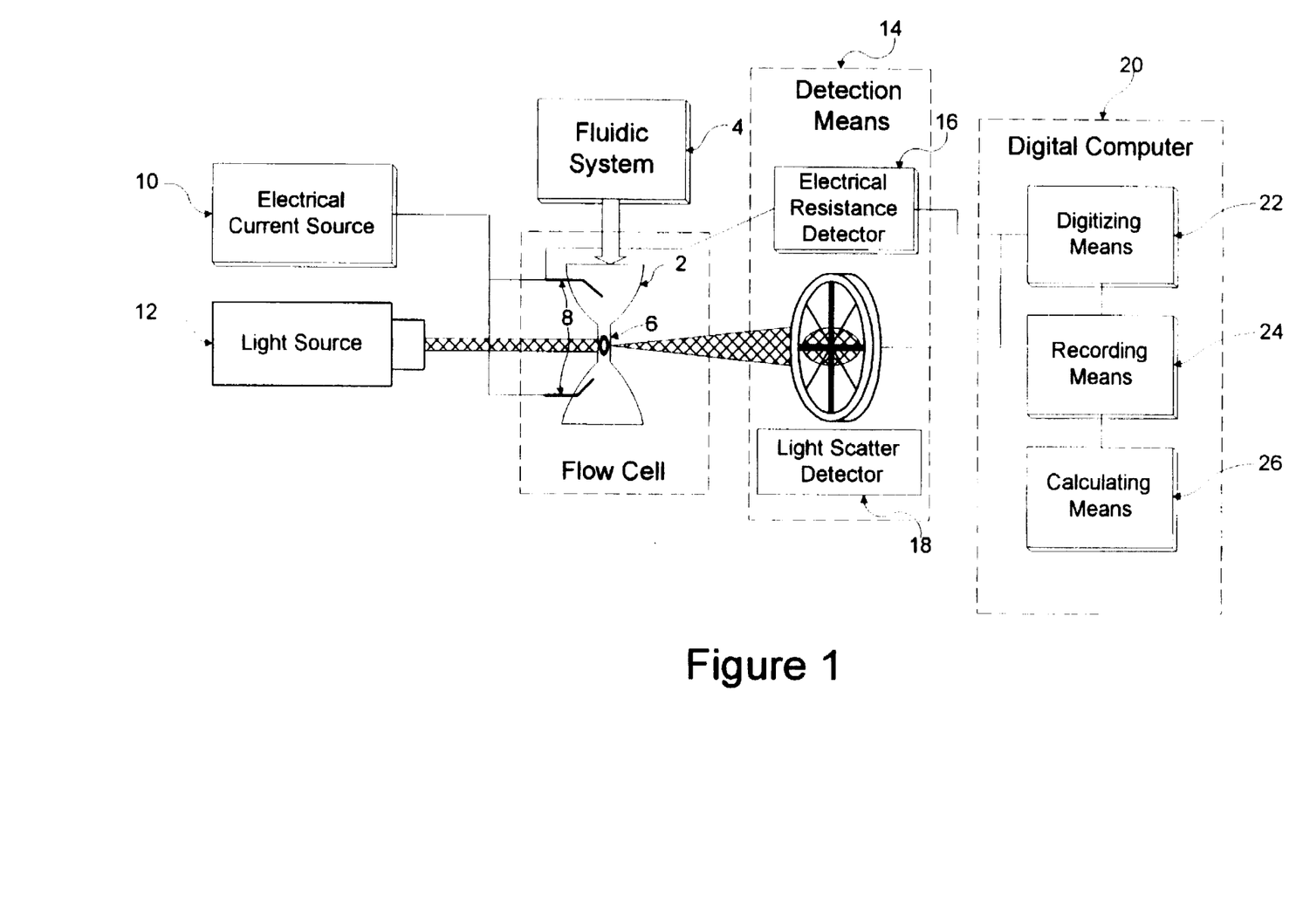
FIG. 1 is a schematic of an apparatus of the present invention.

As shown schematically in FIG. 1, the apparatus of this invention consists of a flow cell 2 attached to a fluidic system 4 that presents a diluted red blood cell sample to the flow cell. The flow cell 2 contains a measuring aperture 6, through which red blood cells flow substantially one at a time. Electrodes 8 are located on each side of the aperture. The electrodes are connected to electrical circuitry 10, capable of establishing an electrical field across the aperture. Preferably, the electrical current source is a direct current source. The aperture is designed to allow for the measurement of light scatter produced by cells flowing within the aperture. A light source 12 is positioned to illuminate a portion of the aperture through which the blood cells flow. Detection means 14 include an electrical resistance detector 16 and a light scatter detector 18 which is positioned on the side opposite the light source to allow for the collection of light scattered over specific angular regions. The electrical resistance and light scatter detectors are connected to a digital computer 20 by digitizing means 22. The digitizing means for converting an analog signal suitable for a digital computer is known to those skilled in the art. The digital computer 20 includes recording means 24 and calculating means 26. The calculating means are used to determine the shape of each cell from the measured electrical and light scatter signals. In addition, the calculating means determines the deformability index and volume of each cell from the same electrical resistance and light scatter signals. The calculating means also compiles statistical values for the red cell population, including the mean, standard deviation and coefficient of variation of the red cell shape and volume.

Figure 2A:
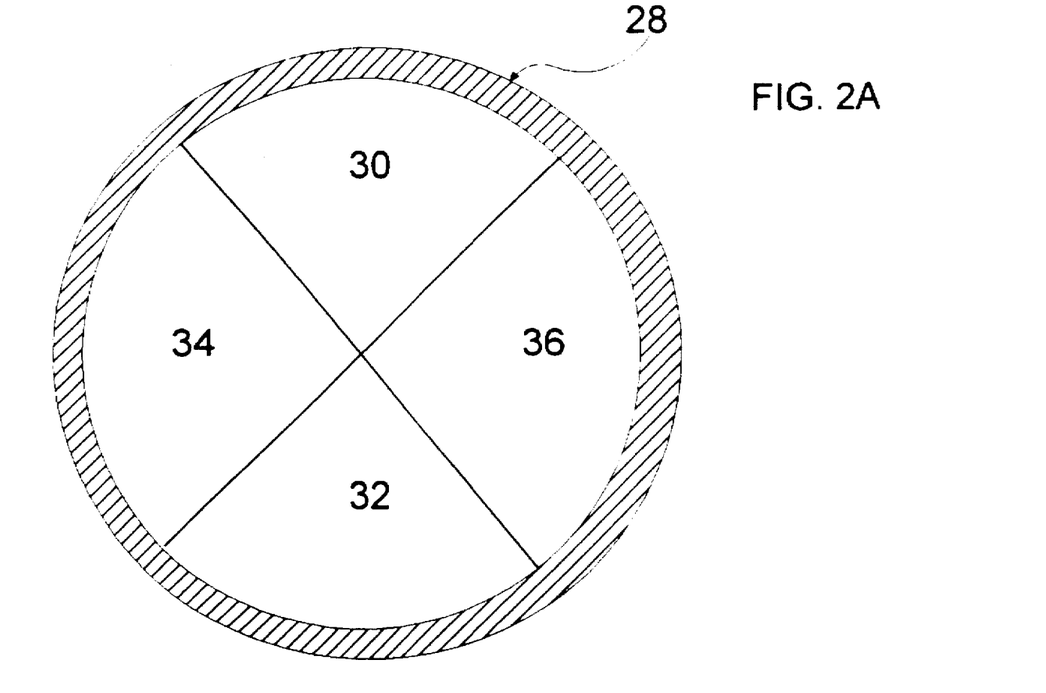
FIG. 2(a) and 2(b) is a schematic of the light scatter detector as described in the preferred embodiment of the invention.
Figure 2B:
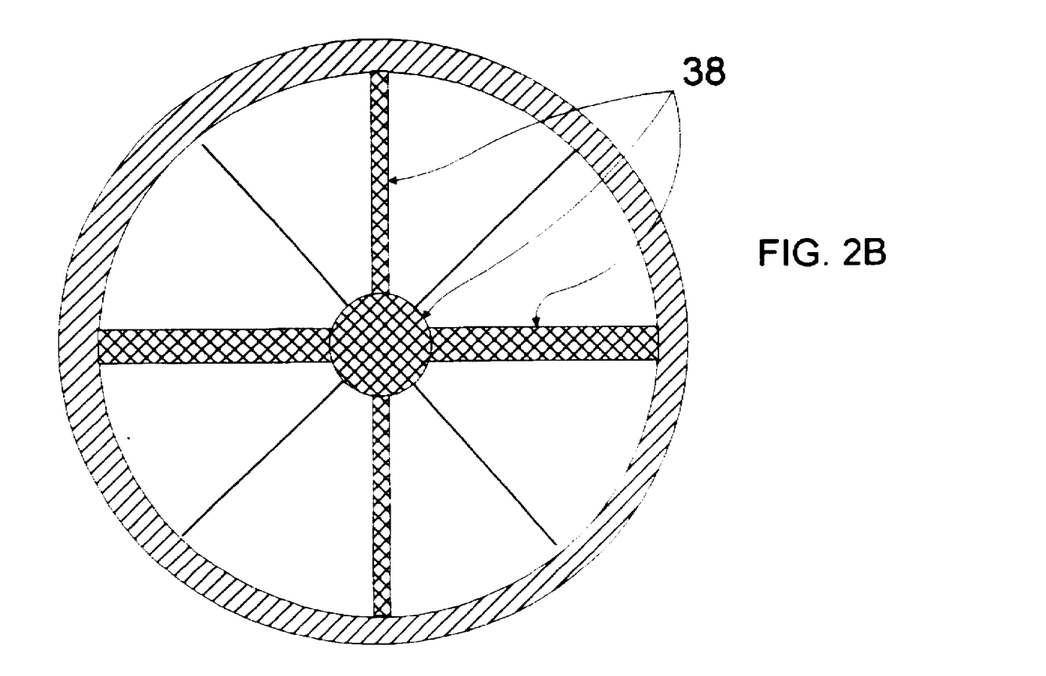

As shown in FIG. 2(a), for the preferred embodiment of the invention, the light scatter detector consists of a four element array 28. Detectors of this or similar configuration are commercially available. The detectors are aligned with the flow cell such that vertical elements 30 and 32 receive light scattered over azimuthal angles from −45° to +45° of the vertical axis of the flow cell, which is parallel to the direction of fluid flow, and the horizontal elements 34 and 36 receive light scatter from azimuthal angles from −45° to +45° of the horizontal axis of the flow cell, which is perpendicular to the direction of fluid flow. As seen in FIG. 2(b), optically opaque masks 38 are applied to the detector in order to prevent unscattered light traveling directly from the laser from striking the central portion of the detector and to limit the collection of scattered light to specific scattering angles. In this embodiment of the apparatus, the detector receives light at scattering angles from about 1 degree to 10 degrees from the axis of incident light. More preferably, the detector receives light at scattering angles from about 1.1 to 7 degrees from the axis of incident light.

Figure 3A:
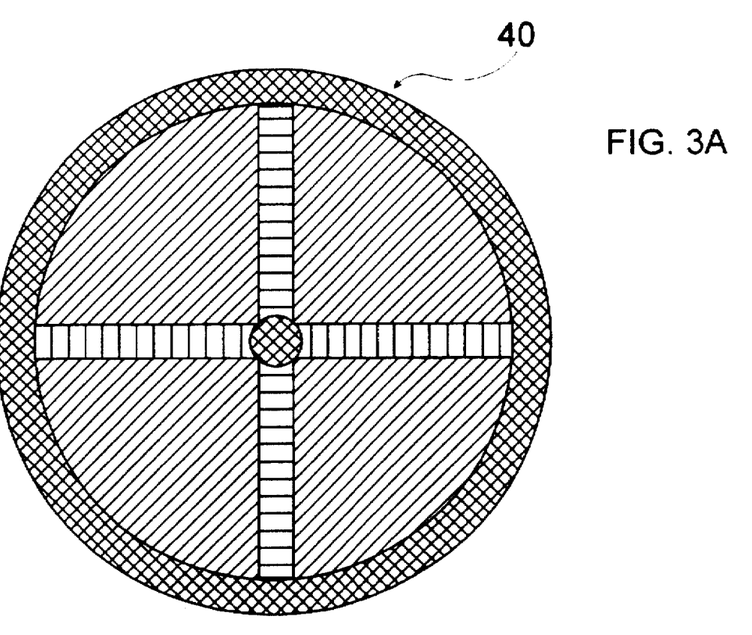
FIG. 3(a) and 3(b) is a schematic of two additional light scatter detector configurations appropriate for the invention.
Figure 3B:
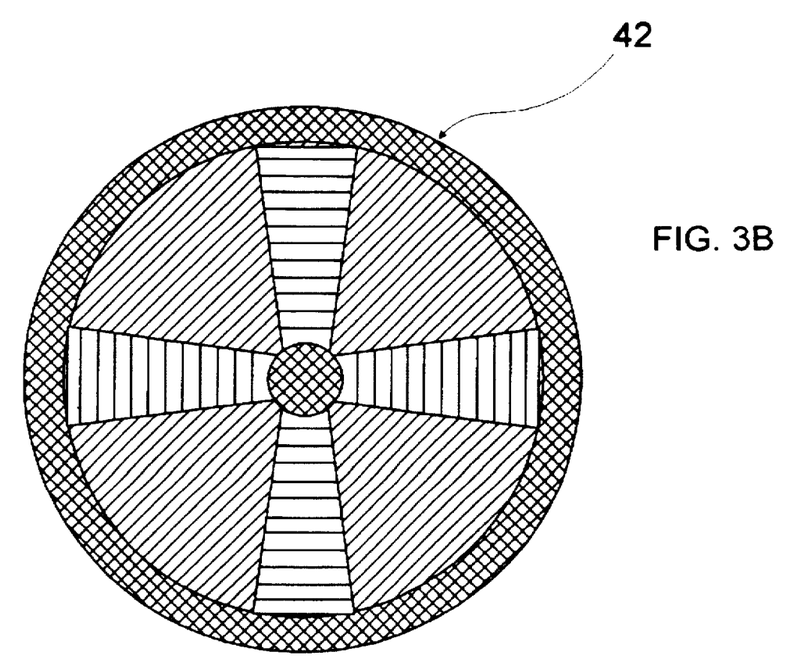

Other configurations of light scatter detectors would be suitable for use in this invention. In one example, only a single vertical element and a single horizontal element are used. While a detector containing a single vertical element and a single horizontal element would be sufficient to produce the measurements described in this invention, the use of four elements as shown in the preferred embodiment allows for precise alignment of the detector in relationship to the illuminating light and the flow cell, and for the collection of additional information to improve the accuracy of the measurement. In a second example, as seen in FIG. 3(a), linear arrays of detector elements 40 arranged horizontally and vertically could be used. Likewise, as seen in FIG. 3(b), a horizontal and vertical arrays of detector elements 42 that increase in width with radial distance could be constructed. This arrangement is called a "Maltese Cross."

Figure 4A:
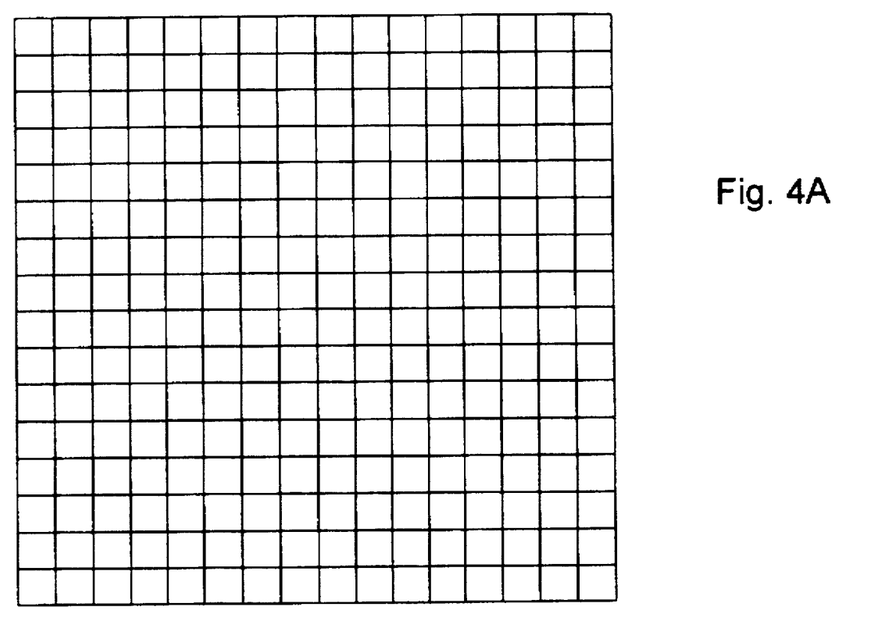
FIG. 4(a) and 4(b) is a schematic of a two dimensional detector array of light detectors elements.
Figure 4B:
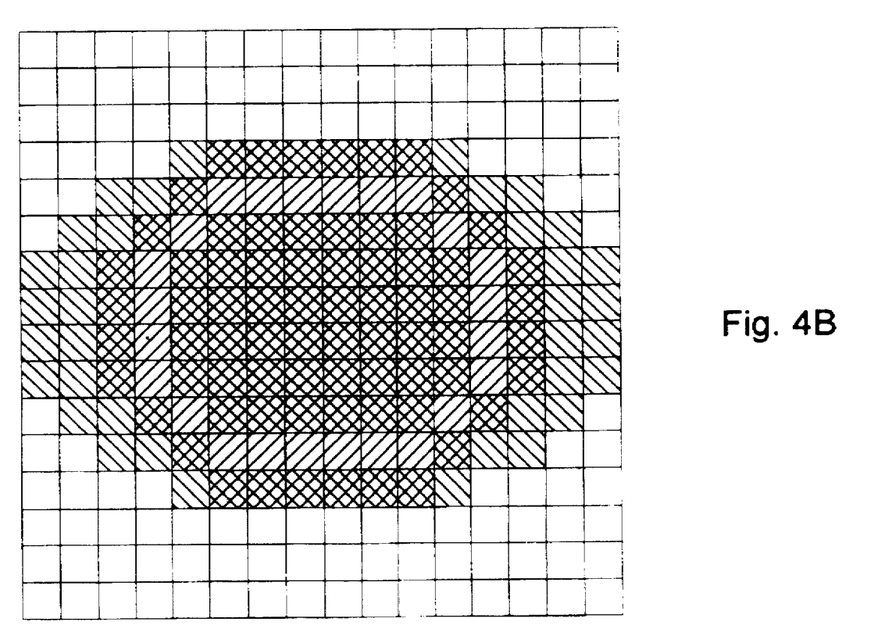
Figure 5A:
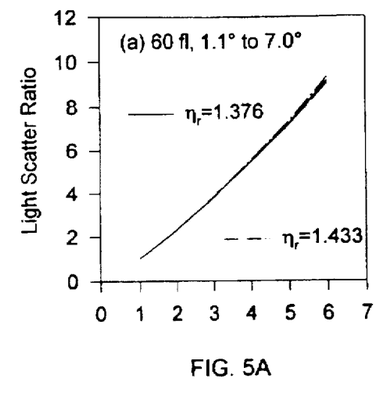
FIG. 5 depicts the result of calculations showing the light scatter from red blood cells of three different cell volumes over ranges of shapes and indices of refraction for light scatter detectors encompassing two different angular regions of collection.
Figure 5B:
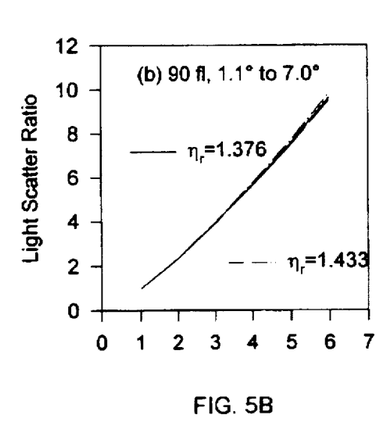
Figure 5C:
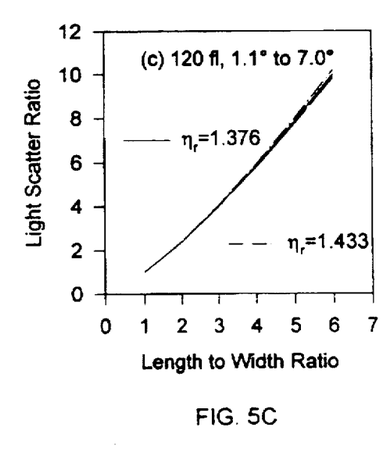
Figure 5D:
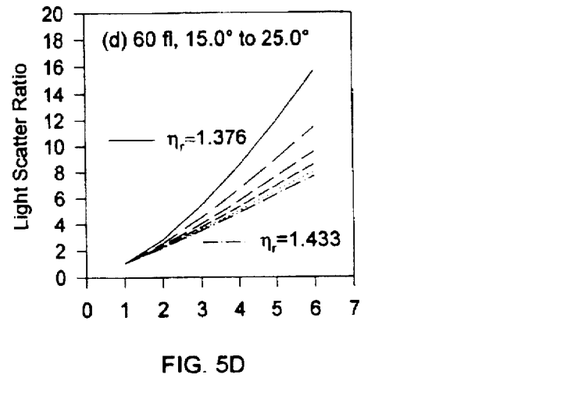
Figure 5E:
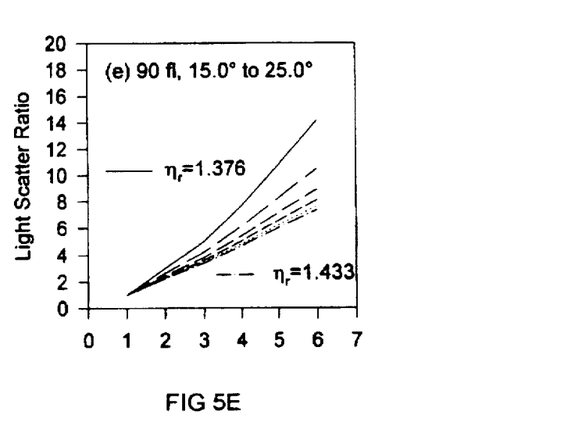
Figure 5F:
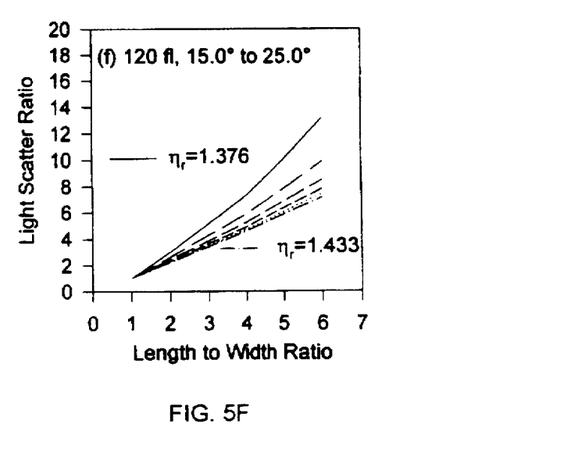

In a further embodiment as depicted in FIG. 4(a), a two-dimensional array of photo-detectors can be used. FIG. 4(b) depicts the light scatter pattern from a deformed red blood cell as measured by this sensing element.

For each of these configurations, the specific angular regions necessary for interpretation of the light scatter asymmetry would be constructed by electronically analyzing the appropriate elements of the array. In addition, other arrangements and numbers of detector elements and optical masks can be constructed that retain the spirit and substance of this invention.

The present invention also provides a method to determine an individual red blood cell shape comprising the steps of forming a stream of individual red blood cells in an electrolyte fluid; flowing said stream of individual red blood cells through a measurement aperture; measuring a change in electrical resistance caused by a red blood cell in said stream of red blood cells flowing through said aperture; deriving a corresponding first signal having an amplitude representative of said change in said electrical resistance caused by said red blood cell flowing through said aperture; illuminating said cell red blood cell with a beam of light when said cell flows through said aperture, which causes said light to be scattered; measuring intensity of said light scattered by said cell at a minimum of two different azimuthal angular regions; deriving a corresponding signal for each angular region, said signal having an amplitude representative of said intensity of light scattered in said angular region; and determining a shape of said red blood cell from said corresponding first signal and said corresponding signal for each angular region.

The shape of each individual red blood cell is determined from the light scatter signals and the direct current resistance measurement by calculating means described below. The shape of the cell is described as the ratio of the length of the cell to its width. This ratio is designated as "m." Thus a sphere, with equal length and width would have a value of "m" equal to 1. Red blood cells are normally capable of deforming to maximum values of "m" equal to approximately 6.

As described previously, light scatter signals are collected along the axes parallel to the fluid flow and perpendicular to the fluid flow. The signals parallel to the direction of fluid flow are called the Vertical Light Scatter or "VLS." The signals perpendicular to the direction of fluid flow are called the Horizontal Light Scatter, or "HLS." The ratio of the Horizontal Light Scatter to the Vertical Light Scatter is designated as the Light Scatter Ratio or "LSR." For the light scatter measurement, the shape ratio m, is a function of the Light Scatter Ratio as well as the volume (V) and index of refraction ($\eta_r$) of the cell. This general relationship is given as:

$$m = f(V, LSR, \eta_r) \quad (1)$$

Thus, to determine the shape ratio, one must determine the volume and index of refraction of the cell in addition to the light scatter ratio. The determination of cell shape from this series of measurements is complicated by the fact that known methods to measure cell volume, such as the electrical resistance method previously disclosed, and index of refraction are also a function of the shape of the cell. Thus, determining cell shape involves simultaneously solving at least three equations. Solutions to these equations are difficult due to their nonlinearity and the coupling between them. It is thus an important advantage, and a significant and unique feature of this invention, to determine specific angular regions of light collection in which the shape determination is largely independent of index of refraction and in a further embodiment the shape determination is also independent of the volume of the cell. This allow ones to reduce the number of measurements, the complexity of the mathematical analysis, the errors associated with the more complex measurement and analysis, and ultimately allows the apparatus and method to be of a form suitable for inclusion into commercial diagnostic instruments. The specific relationship between electrical resistance and cell shape and volume for an electrically non-conducting ellipsoidal particle has been determined by Grover et al. (op. cit.) as:

$$DC = K * Volume * \left( \frac{m^2}{m^2 - 1} - \frac{m * \cosh^{-1} m}{(m^2 - 1)^{3/2}} \right)^{-1}$$

where K is a constant specific for the measurement system, and is determined by a combination of aperture size, fluid conductivity, electrical amplifier gains and other factors.

The appropriate description of light scattering by non-spherical particles of size and index of refraction equivalent to blood cells is known to those skilled in the art of light scatter theory as the "anomalous diffraction theory." This theory requires both that the particle size parameter "$\alpha$," defined as:

$$\alpha = \pi L / \lambda \quad (2)$$

(where $\lambda$ is the wavelength of the incident light; and L is the size of the particle) be greater than 1, and the relative index of refraction, $\eta_{rel}$, to be near 1. The particle size parameter $\alpha$ varies from approximately 15 to 170 for the range of red cells found in normal and abnormal populations and for a light source with a wavelength of 670 nm.

The relative index of refraction, $\eta_{rel}$, is defined as the ratio of the index of refraction of the particle (the red cell, in this case) to the index of refraction of the surrounding medium (typically an electrolytic solutions with $\eta_s = 1.34$). For hemoglobin concentrations from 19 to 49 g/dL, values of $\eta_{rel}$ range from 1.027 to 1.069. Thus both conditions for application of the anomalous diffraction theory are met.

For light scatter as described by this theory, the light scatter intensity distribution, $I_{total}$, can be described as a sum of contributions from Fraunhofer diffraction and transmitted light with refraction (Van de Hulst, H. C., *Light Scattering by Small Particles*, Dover Publications, Inc. New York, N.Y., 1981):

$$I_{total}(\alpha, m, \theta, \phi, \eta_{rel}) = I_{diffracted}(\alpha, m, \theta, \phi) + I_{refracted}(\alpha, \theta, \eta_{rel}) \quad (3)$$

where $\alpha$ and m are the particle size parameter and shape as defined above; $\theta$ is the scattering angle, $\phi$ is the azimuthal angle and $\eta_{rel}$ is the relative index of refraction as defined above. The decomposition of the total intensity into separate diffractive and refractive components allows for the extension of the diffraction term to ellipsoidal particles, which is not possible with previous theories, such as Mie theory. The refraction component has been described by Hodkinson and Greenleaves (Hodkinson, T. R., and Greenleaves, I., "Computations of Light-Scattering and Extinction by Spheres According to Diffraction and Geometrical Optics, and Some Comparisons with the Mie Theory," *Journal of the Optical Society of America*, 53(5), 577–588, 1963) as:

$$I_{refracted}(\alpha,\theta,\eta_{rel}) = 4\alpha^2 \cdot \left(\frac{\eta_{rel}}{\eta_{rel}^2 - 1}\right)^4 \cdot \frac{\left[\eta_{rel} * \cos\left(\frac{\theta}{2}\right) - 1\right]^3 \left[\eta_{rel} - \cos\left(\frac{\theta}{2}\right)\right]^3}{\cos\left(\frac{\theta}{2}\right)\left[\eta_{rel}^2 + 1 - 2\eta_{rel} * \cos\frac{\theta}{2}\right]^2} \left[1 + \frac{1}{\cos^4\left(\frac{\theta}{2}\right)}\right] \quad (4)$$

As derived by Kathuria (Kathuria, Y. P., "Far-Field Radiation Patterns of Elliptical Aperture and its Annulli," *IEEE Trans. Antennas Propag.*, AP-31, 360–363, 1983), the diffraction component for an ellipsoidal particle is:

$$I_{diffracted}(\alpha,m,x,y) = \frac{2\alpha^4}{m^2} * \left[\frac{J_1\left(\sqrt{\alpha^2\frac{x^2}{F^2} + \frac{\alpha^2}{m^2}\frac{y^2}{F^2}}\right)}{\sqrt{\alpha^2\frac{x^2}{F^2} + \frac{\alpha^2}{m^2}\frac{y^2}{F^2}}}\right]^2 \quad (5)$$

Here, $J_1$ is the first order Bessel function of the first kind, x and y are the Cartesian coordinates in the plane perpendicular to the incident light, F is the distance from the particle to the plane on which the diffraction pattern is projected, and, as previously, $\alpha$ is the size parameter in terms of the length of the major axis of the ellipsoid and m is the ratio of the length to the width of the ellipsoid. The above equations can be transformed to a coordinate system in terms of the scattering angle $\theta$ and the azimuthal angle $\phi$ by the following relationships:

$$\theta = \arctan\frac{\sqrt{x^2 + y^2}}{f} \quad (6)$$

$$\phi = \arctan\frac{y}{x} \quad (7)$$

From the theoretical relationships for angular dependency of light scatter intensity given above, total light incident upon a specific detector element is determined by integrating the intensity over the appropriate scattering angle and azimuthal angles. Again, as described previous, this result for the integrated light scatter on a particular angular region is a function of the cell volume and index of refraction as well as shape.

Embodiments of this invention are described that detail specific angular regions that eliminate the general dependence on index of refraction and volume. In FIGS. 5 (*a*), (*b*) and (*c*) the light scatter ratio from angle of collection consisting of scattering angles from 1.1 to 7.0 degrees and azimuthal angles from −45° to +45° of each axis for cell volumes of 60, 90, and 120 femtoliters (fL) respectively are seen. These regions were selected so that, as seen in FIGS. 5 (*a*), (*b*) and (*c*), the LSR is essentially independent on the index of refraction of the cell. In FIGS. 5 (*d*), (*e*) and (*f*) the scattering angles were from 15.0 to 25.0 degrees. Here, the light scatter ratio is dependent upon the index of refraction of the cell, thus making impossible the determination of the shape of the cell from the light scatter ratio without knowledge of the index of refraction. A result independent of the index of refraction is also obtained for scattering angles from 1.1° to 50.0° (data not shown).

Figure 6A:
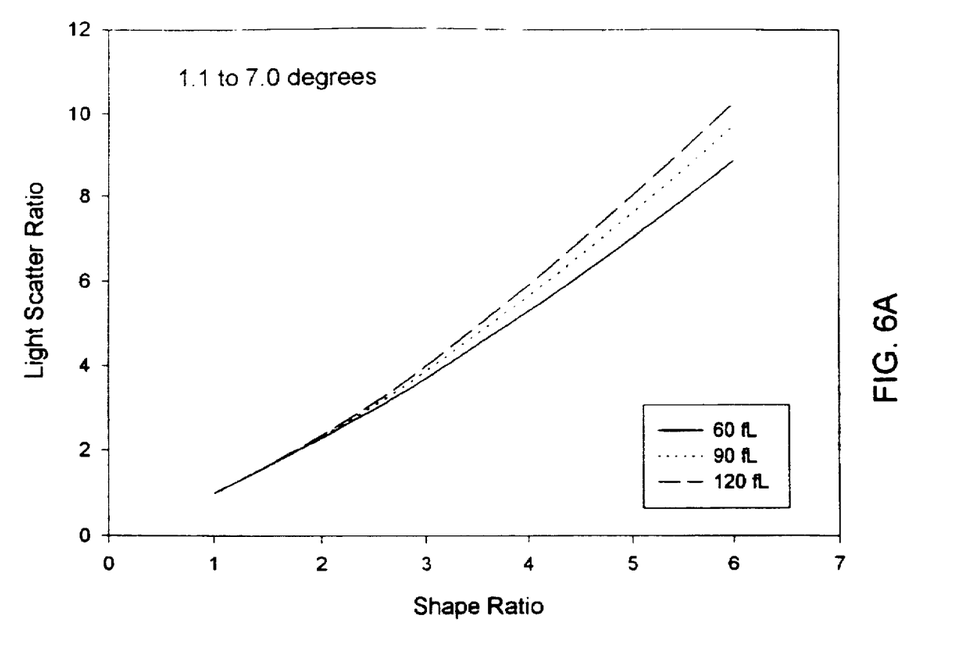
FIG. 6 depicts the calculated sensitivity of the light scatter ratio to differing cell volumes for light scatter detectors encompassing two different angular regions of collection.
Figure 6B:
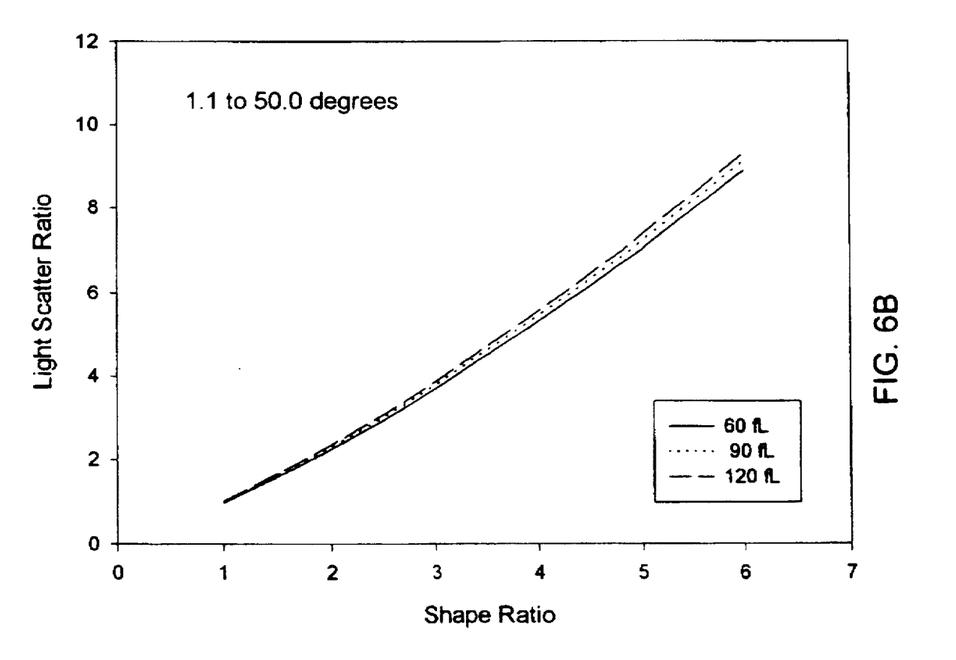
Figure 7A:
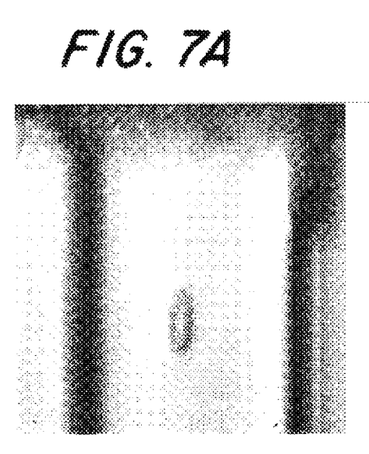
FIG. 7 depicts images of red cells produced by optical imaging means which are used to verify a shape of red cell as determined by the current invention.
Figure 7B:
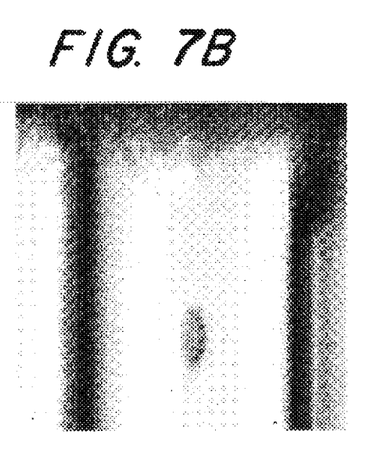
Figure 7C:
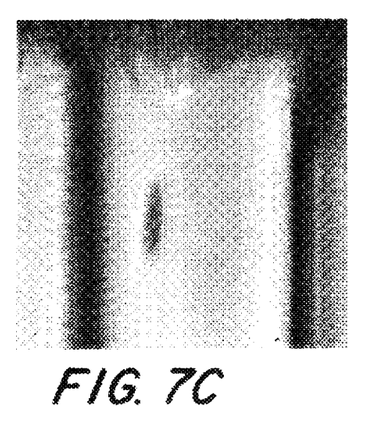
Figure 7D:
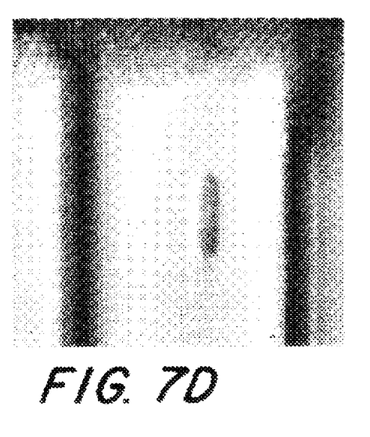

As seen in FIG. 6 (*a*), the dependence of the relationship between light scatter ratio "LSR" and shape ratio "m" is a function of the volume of the cell for the embodiment containing scattering angle from 1.1 to 7.0 degrees and azimuthal angles from −45° to +45° of each axis. However, as seen in FIG. 6(*b*), for the embodiment consisting of scattering angle from 1.1 to 50.0 degrees and azimuthal angles from −45° to +45° of each axis, the light scatter ratio is independent of the volume of the cell.

Thus, in a first embodiment of the present invention (scattering angles from 1.1 to 50.0 degrees and azimuthal angles from −45° to +45° of each axis), the light scatter ratio is independent of the both the index of refraction and the volume of the cell. It is thus possible to determine the shape of the cell just from measurements of the light scatter ratio. In a second preferred embodiment of the invention, when light scatter measurements are made (scattering angles from 1 to 10 degrees and azimuthal angles from −45° to +45° of each axis, preferably 1.1 to 7.0 degrees and azimuthal angles from −45° to +45° of each axis), an additional measurement is made which is indicative of cell volume. While the first embodiment may appear simpler in that the measurement of cell volume is not necessary, attributes of the embodiment are such that it is more difficult and expensive to implement, and thus not the preferred embodiment of this invention. In particular, additional optical elements would be required to collect the wider range of light scatter angles. These elements, consisting of lenses and mounting hardware, increase the cost and complexity of such an embodiment. Whereas the volume of the red cell is normally desired, an embodiment consisting of measuring narrower scattering angles and a measurement of the cell volume is seen as the most practical, economical and useful embodiment of the invention, and thus the preferred embodiment.

For such an embodiment, the measurement of cell volume by the electrical resistance method is the preferred method. Other techniques to determine cell volume are also known to those skilled in the art of cytometry, and could be practiced for this invention. Examples of such techniques would include optical means measuring the axial light loss of the cell within the measurement aperture or optical means measuring the low angle light scatter of the cell within the measurement aperture. Both of these methods, however, are known to be less accurate than electrical resistance sizing for determining cell volume, particularly for non-spherical cells to which this invention is directed, and thus are not the preferred embodiment of the invention.

Figure 8:
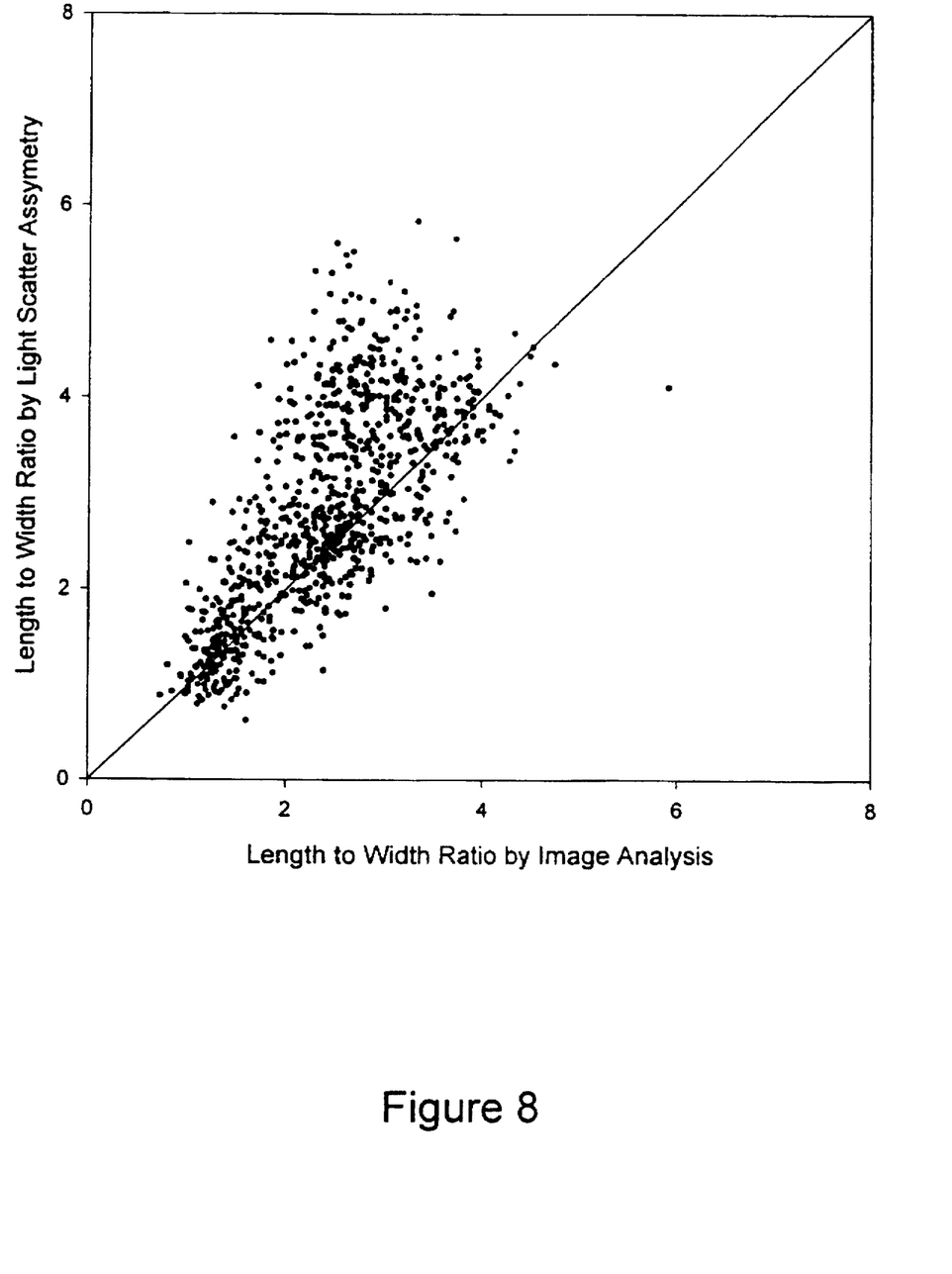
FIG. 8 depicts the correlation between the shape of a red cell, as determined by the current invention, with the shape of the same cell as determined by optical imaging means for a plurality of red cells with shape ratios from 1 to 6.

The determination of the shape of the cell from the light scatter ratio and electrical resistance as described herein has been verified by directly recording video images of red cells simultaneous to these cytometric measurements. FIG. 7 shows examples of such images used in this verification. FIG. 8 shows the comparison of the shape of approximately 500 red cells as determined by the method of this invention with the shape as determined by direct imaging. Cells have been treated by chemical means to produce a range of length to width ratios of from 1 to 6.

In still further embodiments of the invention, arrangements of light scatter detectors other than those detailed in the above embodiment could be employed that provide for an accurate determination of red cell shape. In one embodiment, two-dimensional detector arrays as shown in FIG. 4 could be used. The signals produced by these arrays could be analyzed by a contour method to determine cell shape. In this method, the location of detector elements having the same signal magnitude is identified and the shape of the contour provided by these elements is then determined. As is known to those skilled in the art of light scatter theory, the shape of this contour is equivalent to the shape of the original object from which light is scattered. For the two-dimensional array method, the cost of such an array and associated electronics is substantially more than the preferred embodiment. Thus this embodiment of the invention is not the preferred embodiment.

Additionally, from the determination of the cell shape ratio "m," it is possible to define a deformability index (DI) of the cell which describes the deformation of the cell. This deformation index is defined in terms of the shape ratio "m" as:

$$DI=(m-1)/(m+1) \tag{8}$$

Figure 9:
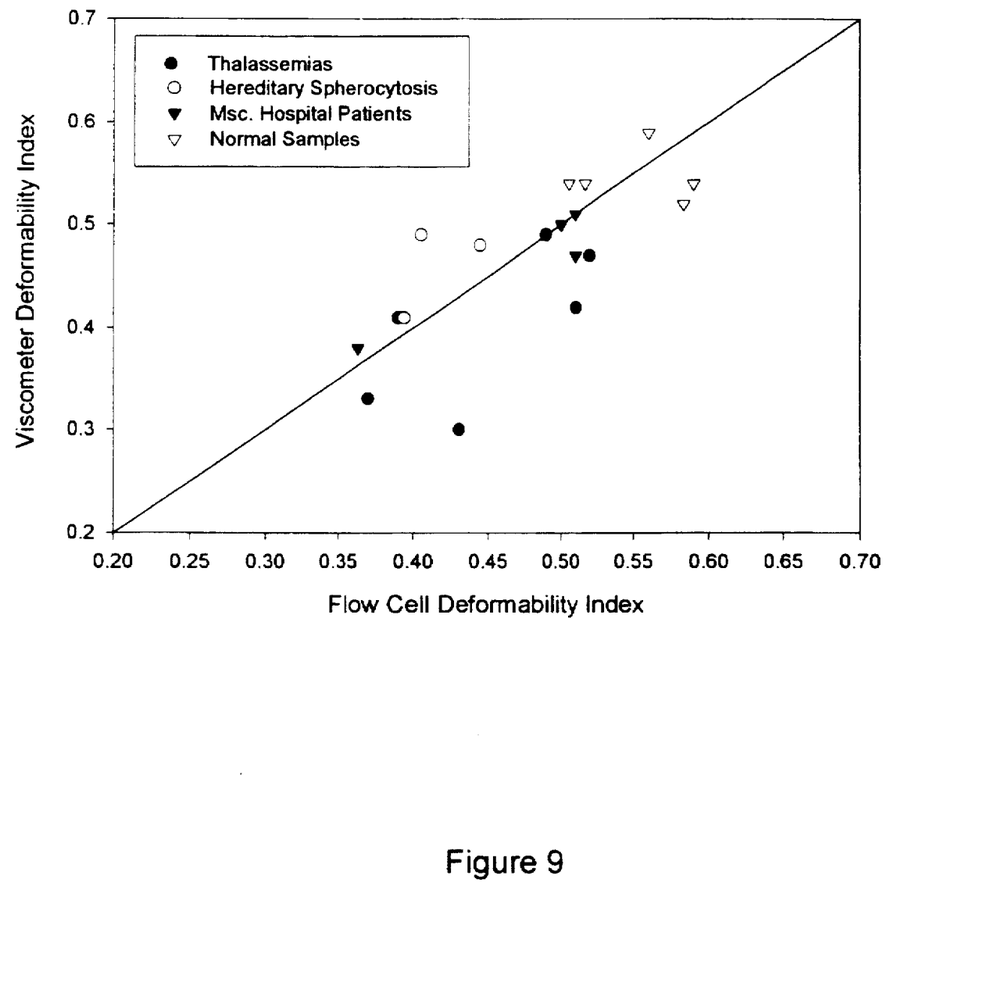
FIG. 9 depicts the correlation of the mean deformability index of red cell samples as obtained from the present invention, with the deformability index as obtained by Ektacytometry.

FIG. 9 shows the comparison of the mean deformability index of samples of blood cells, computed from the cell shape as previously described, with the deformability index as obtained by Ektacytometry. The correlation between these values is seen.

In another embodiments of this invention, other flow cytometric measurements are made simultaneous with the measurement of red cell shape, deformability index and volume as described in this invention. In one embodiment, the additional flow cytometric measurement would be the identification of the subpopulation of reticulocytes within the red cell population. This would be accomplished by staining the red cells with a fluorescent nucleic acid stain and measuring the fluorescence emission at an appropriate wavelength, preferably greater than 400 nanometers. Suitable fluorescent stains include coriphosphene O and thiazole orange. Reticulocyte identification simultaneous to the determination of shape and deformability index would enable the identification of reticulocytes with reduced deformability. Further, correlation of shape and deformability with a maturation state of cells identified as reticulocytes would enable measurement of deformability changes during reticulocyte maturation. In another embodiment, subpopulations of red cells are identified within the greater population of red cells by the use of fluorescently labeled antibodies. An example of such a marker is the monoclonal antibody to the transferrin receptor (CD71).

While the invention has been described in terms of the foregoing specific embodiment thereof, it will be apparent to those skilled in the art that various alternations and modifications may be made to the described embodiment without departing from the scope of the invention, as defined by the appended claims. For example, with appropriate modifications to the flow cell 2, or the resistance pulse sizing aperture 6, the resistance signal measurement may take place upstream from the light scattering measurement, or the two measurements may be made substantially concurrently.

We claim:

1. An apparatus for determining an individual red blood cell shape in a fluid sample, said apparatus comprising:
a) means for forming a stream of individual red blood cells in a fluid, b) means for flowing said stream of individual red blood cells through an aperture, c) means for illuminating said cell red blood cell with a beam of light while said cell flows through said aperture, which causes said light to be scattered, d) means for measuring intensity of said light scattered by said cell at a minimum of two different azimuthal angular regions, said light scatter at said annular regions being independent of the index of refraction of said cell and independent of cell volume, e) means for deriving a corresponding signal for each angular region, said signal having an amplitude representative of said intensity of light scattered in said angular region, and f) means for determining a shape of said red blood cell from said corresponding signal for each angular region.

2. The apparatus of claim 1, wherein said means for measuring intensity of said light scattered by said cell at is at a minimum of two different azimuthal angular regions, whereby said two different azimuthal angular regions comprise an angular region located along an axis parallel to the direction of fluid flow and an angular region located along an axis perpendicular to the direction of fluid flow.

3. The apparatus of claim 2, wherein said means for measuring intensity of said light scattered by said cell is at a minimum of two different azimuthal angular regions, whereby said two different azimuthal angular regions comprise a first angular region having a scattering angle of about 1 to 50 degrees and an azimuthal angle from −45 to +45 degrees of the axis parallel to fluid flow and a second angular region having a scattering angle of about 1 to 50 degrees and an azimuthal angle from −45 to +45 degrees of the axis perpendicular to fluid flow.

4. The apparatus of claim 1, wherein said means for measuring intensity of said light scattered by said cell is at a minimum of two different azimuthal angular regions, whereby said minimum of two different azimuthal angular regions comprise four different azimuthal angular regions wherein two angular regions are located along an axis parallel to the direction of fluid flow and wherein two angular regions are located along an axis perpendicular to the direction of fluid flow.

5. The apparatus of claim 1, wherein said means for measuring intensity of said light scattered by said cell at a minimum of two different azimuthal angular regions comprises a two dimensional array of photo-detector elements.

6. The apparatus of claim 1 which further comprises a means for determining a deformability index of said individual red blood cell.

7. The apparatus of claim 1 which further comprises a means for determining a volume of said individual red blood cell.

8. The apparatus of claim 7, wherein said means for determining a volume of said individual red blood cell comprises determining a volume by measuring a change in electrical resistance caused by said individual red cell within said aperture.

9. The apparatus of claim 7, wherein said means to determining a volume of said individual red blood cell comprises a means for determining individual red blood cell volume by measuring axial light loss of said individual red blood cell within said aperture.

10. The apparatus of claim 7, wherein said means of determining a volume of said individual red blood cell comprises determining a volume by measuring the low angle light scatter of said individual red blood cell within said aperture.

11. The apparatus of claim 1 which further comprises a means for measuring fluorescence of said individual red blood cell.

12. The apparatus of claim 11, wherein said means for measuring fluorescence of said individual red blood cell comprises a means for measuring fluorescence of said individual red blood cell caused by a nucleic acid stain used to identify a reticulocyte subpopulation.

13. The apparatus of claim 11, wherein said means for measuring fluorescence of said individual red blood cell comprises a means for measuring fluorescence of said individual red blood cell caused by a fluorescent surface marker used to identify a red blood cell subpopulation.

14. A method to determine an individual red blood cell shape in a fluid sample comprising:
   a) forming a stream of individual red blood cells in a fluid,
   b) flowing said stream of individual red blood cells through an aperture,
   c) illuminating said red blood cell with a beam of light while said cell flows through said aperture, which causes said light to be scattered,
   d) measuring intensity of said light scattered by said cell at a minimum of two different azimuthal angular regions, said light scatter at said angular regions being independent of the index of refraction of said cell and independent of cell volume,
   e) deriving a corresponding signal for each angular region, said signal having an amplitude representative of said intensity of light scattered in said angular region, and
   f) determining a shape of said red blood cell from said corresponding signal for each angular region.

15. The method of claim 14, wherein said measuring intensity of said light scattered by said cell at is at a minimum of two different azimuthal angular regions, whereby said two different azimuthal angular regions comprise an angular region located along an axis parallel to the direction of fluid flow and an angular region located along an axis perpendicular to the direction of fluid flow.

16. The method of claim 15, wherein said measuring intensity of said light scattered by said cell is at a minimum of two different azimuthal angular regions, whereby said two different azimuthal angular regions comprise a first angular region having a scattering angle of about 1 to 50 degrees and an azimuthal angle from −45 to +45 degrees of the axis parallel to fluid flow and a second angular region having a scattering angle of about 1 to 50 degrees and an azimuthal angle from −45 to +45 degrees of the axis perpendicular to fluid flow.

17. The method of claim 14, wherein said measuring intensity of said light scattered by said cell is at a minimum of two different azimuthal angular regions, whereby said minimum of two different azimuthal angular regions comprise four different angular regions wherein two angular regions are located along an axis parallel to the direction of fluid flow and two angular regions are located along an axis perpendicular to the direction of fluid flow.

18. The method of claim 14 wherein said measuring intensity of said light scattered by said cell at a minimum of two different azimuthal angular regions comprises using a two dimensional array of photo-detector elements.

19. The method of claim 14 which further comprises determining a deformability index of said individual red blood cell.

20. The method of claim 14 which further comprises determining a volume of said individual red blood cell.

21. The method of claim 20, wherein said determining a volume of said individual red blood cell comprises determining a volume by measuring a change in electrical resistance caused by said red cell within said aperture.

22. The method of claim 20, wherein said determining a volume of said individual red blood cell comprises determining a volume by measuring axial light loss of said red blood cell within said aperture.

23. The method of claim 20, wherein said determining a volume of said individual red blood cell comprises determining a volume by measuring low angle light scatter of said red blood cell within said aperture.

24. The method of claim 14 which further comprises measuring fluorescence of said individual red blood cell.

25. The method of claim 20, wherein said measuring fluorescence of said individual red blood cell comprises measuring fluorescence caused by a nucleic acid stain used to identify a reticulocyte subpopulation.

26. The method of claim 20, wherein said measuring fluorescence of said individual red blood cell comprises measuring fluorescence caused by a fluorescent surface marker used to identify a red blood cell subpopulation.

27. Apparatus for determining an individual red blood cell shape in a fluid sample, said apparatus comprising:
   a) means for forming a stream of individual red blood cells in an electrolyte fluid;
   b) means for flowing said stream of individual red blood cells through an aperture,
   c) means for providing an electrical current flow through said aperture and means for measuring the resistance of said aperture to said current flow;
   d) means for measuring a change in said electrical resistance caused by a red blood cell in said stream of red blood cells flowing through said aperture,
   e) means for deriving a corresponding first signal having an amplitude representative of said change in said electrical resistance caused by said red blood cell flowing through said aperture,
   f) means for illuminating said red blood cell with a beam of light while said cell flows through said aperture, which causes said light to be scattered,
   g) means for measuring intensity of said light scattered by said cell at a minimum of two different azimuthal angular regions, said light scatter at said angular regions being independent of the index of refraction of said cell,
   h) means for deriving a corresponding signal for each angular region, said signal having an amplitude representative of said intensity of light scattered in said angular region, and
   i) means for determining a shape of said red blood cell from said corresponding first signal and said corresponding signal for each angular region.

28. The apparatus of claim 27, wherein said means for providing an electrical current flow comprises a means for providing a direct current electrical flow.

29. The apparatus of claim 27, wherein said means for measuring intensity of said light scattered by said cell at a minimum of two different azimuthal angular regions whereby said two different azimuthal angular regions comprise a first angular region located along an axis parallel to the direction of fluid flow and a second angular region located along an axis perpendicular to the direction of fluid flow.

30. The apparatus of claim 29, wherein said first angular region comprises a scattering angle of about 1 to 10 degrees and an azimuthal angle from −45 to +45 degrees of the axis parallel to fluid flow and said second angular region comprises a scattering angle of about 1 to 10 degrees and an azimuthal angle from −45 to +45 degrees of the axis perpendicular to fluid flow.

31. The apparatus of claim 27, wherein said means for measuring intensity of said scattered light comprises a two dimensional array of photo-detector elements.

32. The apparatus of claim 27, which further comprises a means for determining a deformability index of said red blood cell.

33. The apparatus of claim 27, which further comprises a means for measuring fluorescence of said individual red blood cell.

34. The apparatus of claim 27, wherein said means for measuring fluorescence of said individual red blood cell comprises means for measuring fluorescence of said individual red blood cell caused by a nucleic acid stain used to identify a reticulocyte subpopulation.

35. The apparatus of claim 27, wherein said means for measuring fluorescence of said individual red blood cell comprises means for measuring fluorescence of said individual red blood cell caused by a fluorescent surface marker used to identify a red blood cell subpopulation.

36. A method to determine an individual red blood cell shape comprising the steps of:
   a) forming a stream of individual red blood cells in an electrolyte fluid;
   b) flowing said stream of individual red blood cells through an aperture;
   c) providing an electrical current flow through said aperture and measuring the resistance of said aperture to said current flow;
   d) measuring a change in electrical resistance caused by a red blood cell in said stream of red blood cells flowing through said aperture;
   e) deriving a corresponding first signal having an amplitude representative of said change in said electrical resistance caused by said red blood cell flowing through said aperture;
   f) illuminating said cell red blood cell with a beam of light while said cell flows through said aperture, which causes said light to be scattered;
   g) measuring intensity of said light scattered by said cell at a minimum of two different azimuthal angular regions, said light scatter at said angular regions being independent of the index of refraction of said cell;
   h) deriving a corresponding signal for each angular region, said signal having an amplitude representative of said intensity of light scattered in said angular region; and
   i) determining a shape of said red blood cell from said corresponding first signal and said corresponding signal for each angular region.

37. The method of claim 36, wherein said change in electrical resistance comprises a change in direct current electrical resistance.

38. The method of claim 36, wherein said two different azimuthal angular regions comprise an angular region located along an axis parallel to the direction of fluid flow and an angular region located along an axis perpendicular to the direction of fluid flow.

39. The method of claim 38, wherein said azimuthal angular regions comprise a first angular region having a scattering angle of about 1 to 10 degrees and an azimuthal angle from −45 to +45 degrees of the axis parallel to fluid flow and a second angular region having a scattering angle of about 1 to 10 degrees and an azimuthal angle from −45 to +45 degrees of the axis perpendicular to fluid flow.

40. The method of claim 32, wherein measuring intensity of said light scatter by said cell is measured at four different angular regions comprising two angular regions which are located along an axis parallel to the direction of fluid flow and two angular regions which located along an axis perpendicular to the direction of fluid flow.

41. A method of claim 32, wherein measuring intensity of said scattered light comprises measuring intensity of said scattered light with a two dimensional array of photo-detector elements.

42. The method of claim 32, which further comprises measuring fluorescence of said red blood cell.

43. The method of claim 42, which further comprises adding a nucleic acid stain that is used to identify a reticulocyte subpopulation to said red blood cell to before measuring fluorescence of said red blood cell.

44. The method of claim 42, which further comprises adding a fluorescently tagged monoclonal antibody that is used to identify a red blood cell subpopulation to said red blood cell, before measuring fluorescence of said red blood cell.

45. The method of claim 36, which further comprises determining a deformability index for said red blood cell.

* * * * *